US00PP35278P2

(12) United States Plant Patent
Olesen

(10) Patent No.: US PP35,278 P2
(45) Date of Patent: Jul. 25, 2023

(54) ROSE PLANT NAMED 'POULPAL093'

(50) Latin Name: *Rosa hybrida*
Varietal Denomination: Poulpal093

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/803,615

(22) Filed: Sep. 13, 2022

(30) Foreign Application Priority Data

Sep. 24, 2021 (QZ) ..... PBR 2021/2362

(51) Int. Cl.
*A01H 5/02* (2018.01)
*A01H 6/74* (2018.01)

(52) U.S. Cl.
USPC ..... Plt./146
CPC ..... *A01H 6/749* (2018.05)

(58) Field of Classification Search
USPC ..... Plt./146
See application file for complete search history.

(56) References Cited

PUBLICATIONS https://www.poulsenroser.dk/en/roses/ShowProduct/53422; Nov. 15, 2022; 2 pages.*
CPVO Application Consultation Version 4.2.48 for 'Poulpal093'; Nov. 15, 2022; 2 pages.*

* cited by examiner

*Primary Examiner* — Kent L Bell

(57) ABSTRACT

A new garden rose plant of the Compact Floribunda class which has abundant, apricot flowers and attractive foliage. This new and distinct variety has shown to be uniform and stable in the resulting generations from asexual propagation.

2 Drawing Sheets

Botanical designation: *Rosa hybrida.*
Variety denomination: 'Poulpa1093'.

This application claim priority to Plant Breeder's Rights Application Number 2021,2362, which was filed at the Community Plant Variety Rights Office (CPVO) in the European Union on Sep. 24, 2021, the contents of which are hereby incorporated by reference for all purposes.

The applicant in the above referenced Plant Breeder's Rights application, Paulsen Roser A/S, obtained the claimed plant directly from the Inventor Morgens Nyegaard Olesen.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpa1093', originated as a single seedling from the stated cross.

The new variety may be distinguished from its male pollen parent and female seed parent primarily by the following characteristics. The male pollen parent plant has near white flowers while the new variety has apricot flowers. The female seed parent plant has the growth habit of a climber while the new variety grows upright and compact.

The objective of the hybridization of this rose variety was to create a new and distinct variety with unique qualities, such as:

1. Uniform and abundant apricot flowers;
2. Vigorous, but compact growth when propagated on its own roots;
3. Exceptional disease resistance.

This combination of qualities is not present in previously available commercial cultivars of this type, known to the inventor, and distinguish 'Poulpa1093' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpa1093' was selected in the spring of 2011 by the inventor as a single plant from the progeny of the aforementioned hybridization.

Asexual reproduction of 'Poulpa1093' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpa1093' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpa1093'.

Specifically illustrated in FIG. 1 of the drawings are open flowers viewed from above and the side, flower petals and sepals detached, revealing reproductive flower parts, and a flower bud.

Figure 1:
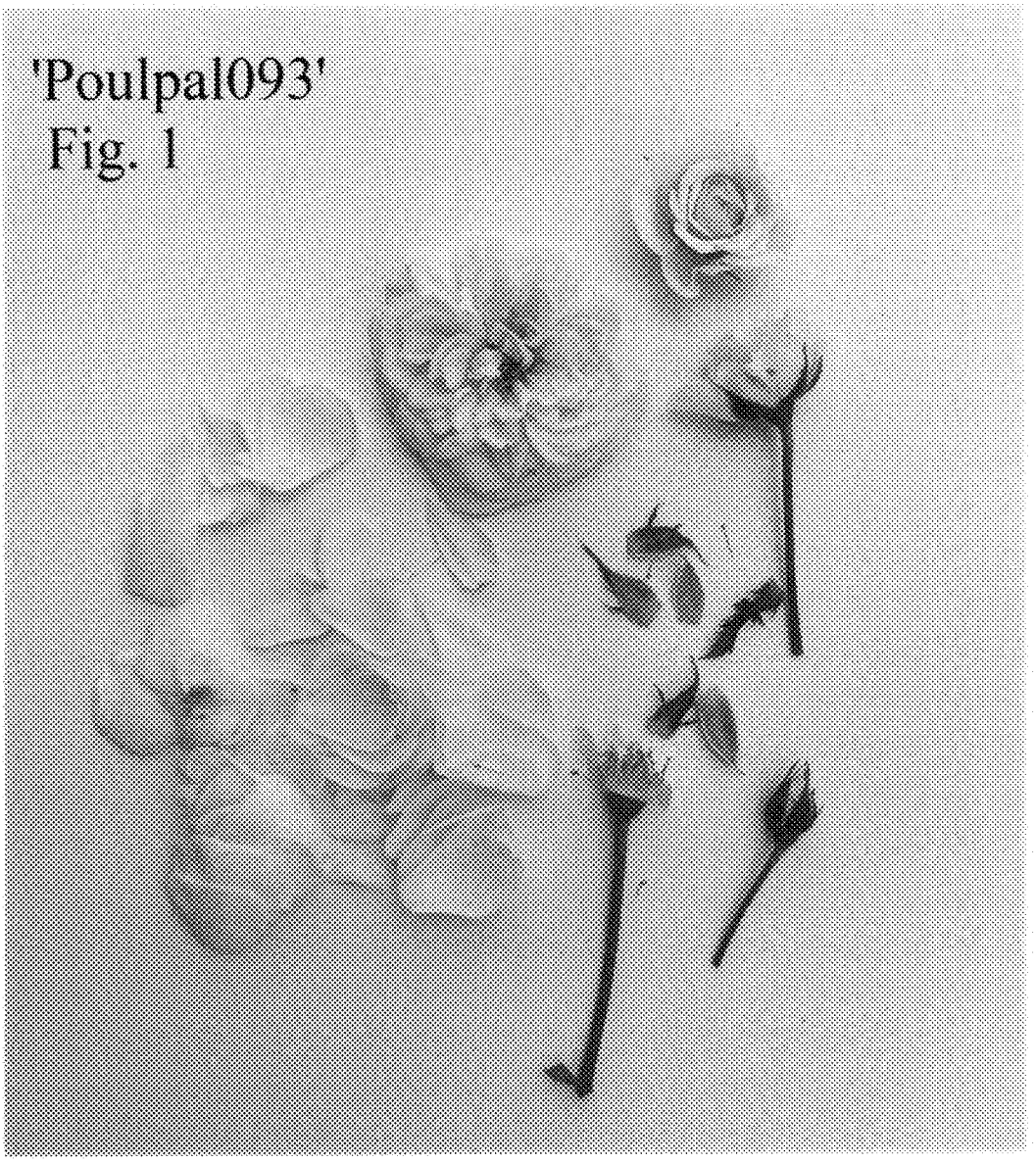
Figure 2:
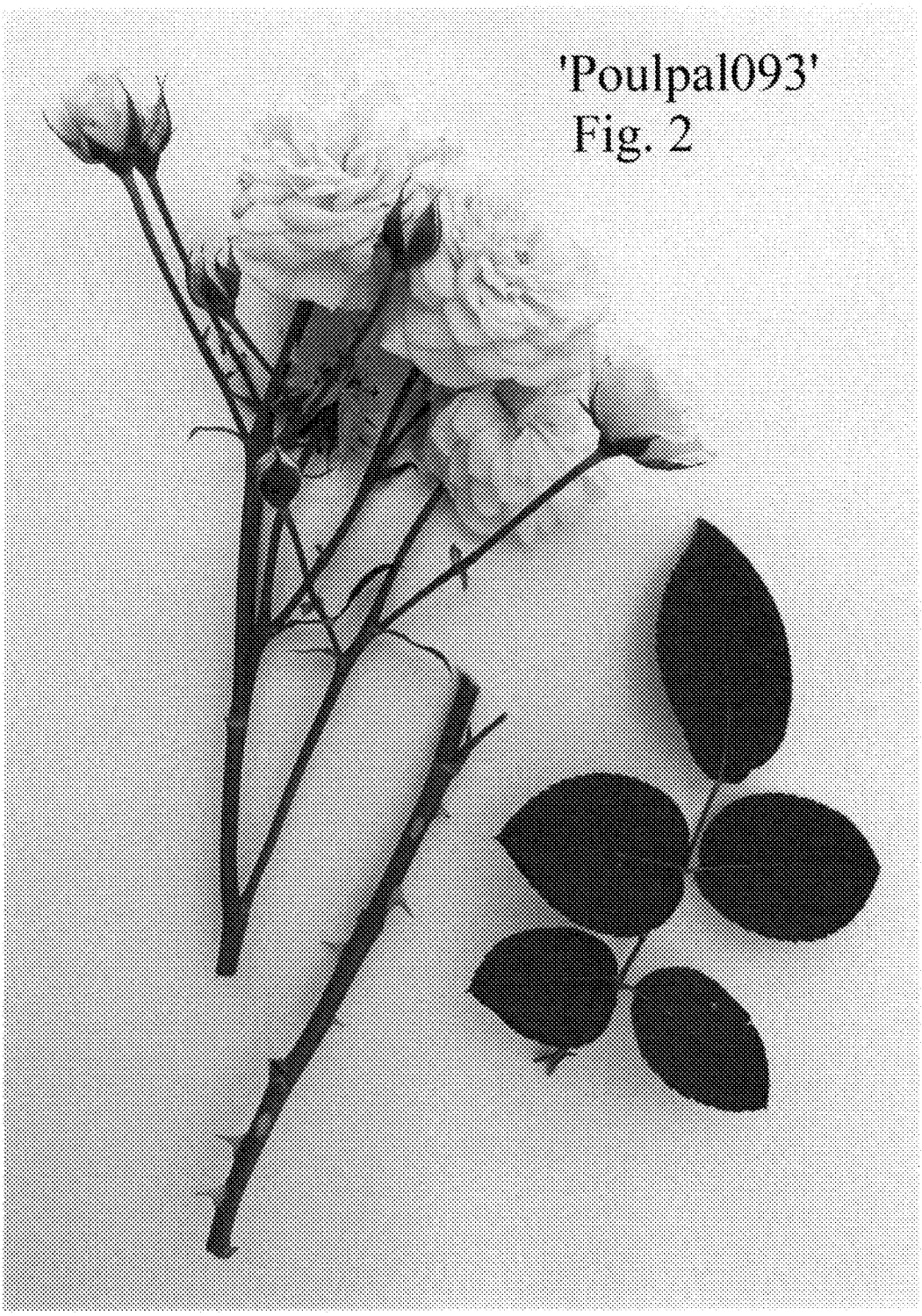

Specifically illustrated in FIG. 2 of the drawings are a mature leaf, bare stem, and a cluster of flowers on a branch. Plants shown are 2 years of age.

DETAILED DESCRIPTION OF THE VARIETY

The following is a description of 'Poulpa1093', observed in its growth in a glass house located in Odense Denmark. Observed plants are 6 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpa1068', U.S. Plant Pat. No. 28,930 are compared to the claimed plant 'Poulpa1093'. The comparison variety has a general tonality of flower colour of a blend of Yellow-Orange Group 23C and Orange Group 29A. The claimed plant has a general tonality of flower colour of Yellow-Orange Group 19B. The claimed plant has a flower petal count of 98 petals, while the comparison variety has a flower petal count of 25 petals.

Flower and Flower Bud

Blooming habit: Continuous.

Flower bud:

- *Size: Upon opening,* 19 mm in length from base of receptacle to end of bud. Bud diameter is 11 mm.
- *Bud form.*—Globose.
- *Bud color.*—As sepals divide petals are Yellow Group 12C.
- *Sepal inner surface.*—Color: Yellow-Green Group 146A. Surface: Lightly pubescent.
- *Sepal outer surface.*—Color: Yellow-Green Group 147C. Texture: Smooth.
- *Sepal shape.*—General: Sepals are typically subulate or lanceolate. Apex: Cirrhose. Base: Flat at union with receptacle.
- *Sepal margin.*—Margins have strong foliaceous appendages on three of the five sepals.
- *Sepal size.*—24 mm long, 7 mm wide.
- *Receptacle.*—Texture: Smooth. Size: 5 mm in height, 7 mm wide. Color: Yellow-Green Group 144A. Shape: Campanulate.
- *Pedicel.*—Surface: Smooth. Length: About 55 mm. Diameter: 2 mm on average. Color: Yellow-Green Group 144A. Strength: Strong.
- *Peduncle.*—Length: Varying from 4 to 12 cm. Diameter: About 3 mm. Color: Yellow-Green Group 144A. Texture: Smooth.

Flower bud development: Flower buds are borne in clusters of 3 to 9 flower buds per stem. Development as a panicle.

Flower bloom:

- *Fragrance.*—Very strong, citrus perfume.
- *Duration.*—The blooms have a duration on the plant of approximately 14 days. Petals fall cleanly away from plant after flowers have fully matured.
- *Size.*—Flower diameter is 60 mm when open. Flower depth is 29 mm.
- *Flower shape.*—Initially a semi-open cup, very double flower, with petals that curve out from the center. After flowers have matured, they resemble a pompon.
- *Shape of flower, side view.*—The upper portion is initially flat, becoming convex. The lower portion is concave.

Petalage: Under normal conditions, flowers have about 98 petals.

General tonality of flower: Open flowers are Yellow-Orange Group 19B.

Petal color:

- *Upon opening, outer petals.*—Upper surface: White Group 155B. At the basal zone Yellow Group 12C. Lower surface: At the basal zone Yellow-Orange Group 22B. At the middle and marginal zone White Group 155B.
- *Upon opening, inner petals.*—Upper surface: Base Yellow Group 12A. Middle zone Yellow Group 13C, and marginal White Group 155B. Lower surface: Yellow-Orange Group 16C with marginal White Group 155A. Basal petal spots: No distinctive coloration at the petal base upon opening.
- *After opening, outer petals.*—Upper surface: White Group 155D. Lower surface: White Group 155D with light intonations of Red Group 56C.
- *After opening, inner petals.*—Upper surface: White Group 155D. Lower surface: White Group 155D with light intonations of Red Group 56C. Basal petal spots: No distinctive coloration at the petal base after opening.

Petals:

- *Petal reflex.*—Strong.
- *Margin.*—Entire and uniform. Very light undulations at the apex.
- *Shape.*—Broad and elliptic. Apex shape: Rounded. Base shape: Acute.
- *Size.*—30 mm (l)×26 mm (w).
- *Texture.*—Smooth.
- *Thickness.*—Average.

Petaloids:

- *Size.*—15 mm (l) by 6 mm (w).
- *Quantity.*—About 30.
- *Shape.*—Elliptical with an acute base and rounded apices.
- *Color.*—White Group 155D with Yellow Group 8A at basal zone point of attachment.

Reproductive flower parts:

- *Pollen.*—None observed.
- *Anthers.*—Size: 1.5 mm in length. Color: Greyed-Orange Group 163A. Quantity: 35 on average.
- *Filaments.*—Color: Yellow Group 13B. Length: 6 mm.
- *Pistils.*—Length: 10 mm. Quantity: 26 on average.
- *Stigmas.*—Color: Greyed-Yellow Group 160B.
- *Styles.*—Color: Red-Purple Group 58B.
- *Location of stigmas.*—Superior in location relative to the length of the filaments and the height of the anthers.
- *Hips.*—None Observed.

Plant

Plant growth: Upright. Plants are about 90 cm in height, and 40 cm wide.

Stems:

- *Color of juvenile growth.*—Yellow-Green Group 144B.
- *Color of mature growth.*—Yellow-Green Group 144A.
- *Length.*—Canes are about 25 cm from the base of the plant to the flowering portion.

*Diameter.*—About 5 mm.

*Internodes.*—On mature canes about 40 mm between nodes.

*Surface texture.*—Young wood: Smooth. Older wood: Smooth.

Long prickles:

*Incidence.*—About 8 prickles per 10 cm of stem.

*Size.*—Average length of prickles on mature stems is 10 mm.

*Shape.*—Upper portion is linear. Lower portion is concave.

*Color.*—Juvenile prickles: Greyed-Yellow Group 160C. Mature prickles: Greyed-Yellow Group 160C.

Plant foliage:

*Compound leaf.*—170 mm (l)×120 (w).

*Quantity.*—2 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 147B.

Plant leaves and leaflets:

*Stipules.*—Size: 10 mm long, 3 mm wide. Quantity: 2 per compound leaf. Shape: Linear, slightly broad based with outward extending apices. Margins: Finely serrated. Color: Yellow-Green Group 146B.

*Petiole.*—Length: 30 mm. Diameter: 2 mm. Upper surface color: Yellow-Green Group 144A. Lower surface color: Yellow-Green Group 144A.

*Rachis.*—Length: About 30 mm. Upper surface color: Yellow-Green Group 144A. Lower surface color: Yellow-Green Group 144A.

*Leaflet.*—Quantity: Normally 5 leaflets. Margins: Serrated. Size: Terminal leaflets are about 74 mm long, 46 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phraginidium* spp., black spot *Diplocarpon rosae*, and *Botiytis cinerea* under normal growing conditions.

Cold hardiness: The variety is tolerant to USDA Cold Hardiness Zone 6.

Heat tolerance: The variety has been found to be suitable for climate conditions found in The American Horticulture Society heat zone 7.

Pest resistance: The variety is susceptible to any insect pest normally associated with the species.

I claim:

1. A new and distinct variety of rose plant named 'Poulpa1093' substantially as described and illustrated herein.

* * * * *

'Poulpal093'

'Poulpal093'